(12) United States Patent
Irion et al.

(10) Patent No.: US 12,167,839 B2
(45) Date of Patent: Dec. 17, 2024

(54) ENDOSCOPE AND CLEANING INSTRUMENT FOR AN ENDOSCOPE

(71) Applicant: KARL STORZ SE & Co. KG, Tuttlingen (DE)

(72) Inventors: Klaus Irion, Tuttlingen (DE); Uwe Bacher, Tuttlingen (DE); Michael Sauer, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 756 days.

(21) Appl. No.: 17/375,629

(22) Filed: Jul. 14, 2021

(65) Prior Publication Data

US 2021/0338071 A1    Nov. 4, 2021

Related U.S. Application Data

(62) Division of application No. 15/596,835, filed on May 16, 2017, now Pat. No. 11,089,952.

(30) Foreign Application Priority Data

May 17, 2016 (DE) .......................... 102016109066.2

(51) Int. Cl.
| | |
|---|---|
| *A61B 1/00* | (2006.01) |
| *A61B 1/018* | (2006.01) |
| *A61B 1/05* | (2006.01) |
| *A61B 1/06* | (2006.01) |
| *A61B 1/12* | (2006.01) |
| *A61B 1/313* | (2006.01) |

(52) U.S. Cl.
CPC .......... *A61B 1/126* (2013.01); *A61B 1/00091* (2013.01); *A61B 1/018* (2013.01); *A61B 1/05* (2013.01); *A61B 1/06* (2013.01); *A61B 1/3132* (2013.01)

(58) Field of Classification Search
CPC ..... A61B 1/126; A61B 1/00091; A61B 1/018; A61B 1/05; A61B 1/122; A61B 1/00142
See application file for complete search history.

(56) References Cited

U.S. PATENT DOCUMENTS

| | | | | |
|---|---|---|---|---|
| 4,867,138 | A | * | 9/1989 | Kubota .............. A61B 1/00098 600/105 |
| 4,972,827 | A | * | 11/1990 | Kishi ..................... A61B 1/313 600/114 |
| 5,025,778 | A | | 6/1991 | Silverstein et al. |
| 5,083,549 | A | | 1/1992 | Cho et al. |
| 5,207,213 | A | | 5/1993 | Auhll et al. |
| 5,334,150 | A | | 8/1994 | Kaali |

(Continued)

FOREIGN PATENT DOCUMENTS

| | | |
|---|---|---|
| CH | 698893 B1 | 11/2009 |
| EP | 0434793 A1 | 7/1991 |

(Continued)

*Primary Examiner* — Timothy J Neal
(74) *Attorney, Agent, or Firm* — McGlew and Tuttle, P.C.

(57) ABSTRACT

An endoscope (10) includes an endoscope shaft (13), with a distal shaft portion (20), a central shaft portion (30) and a proximal shaft portion (40), and a light admission face (11) at the distal shaft portion (20). A cross section of the central shaft portion (30) is smaller than the cross section of the distal shaft portion (20) and smaller than the cross section of the proximal shaft portion (40).

12 Claims, 4 Drawing Sheets

(56) References Cited

U.S. PATENT DOCUMENTS

| | | |
|---|---|---|
| 5,392,766 A | 2/1995 | Masterson et al. |
| 5,514,084 A | 5/1996 | Fisher |
| 5,630,795 A * | 5/1997 | Kuramoto .......... A61B 1/00137 |
| | | 604/35 |
| 6,387,043 B1 | 5/2002 | Yoon |
| 6,878,106 B1 | 4/2005 | Herrmann |
| 2003/0040657 A1 | 2/2003 | Yamaya et al. |
| 2003/0093088 A1 | 5/2003 | Long et al. |
| 2004/0102804 A1 | 5/2004 | Chin |
| 2004/0204629 A1 | 10/2004 | Knapp |
| 2007/0118019 A1 | 5/2007 | Mitani et al. |
| 2007/0244362 A1 * | 10/2007 | El-Hachem .......... A61B 1/0055 |
| | | 600/128 |
| 2008/0200765 A1 * | 8/2008 | Mondschein ........ A61B 1/3132 |
| | | 600/157 |
| 2008/0234547 A1 | 9/2008 | Irion et al. |
| 2009/0231419 A1 | 9/2009 | Bayer |
| 2010/0185145 A1 | 7/2010 | Pepper et al. |
| 2013/0238789 A1 | 9/2013 | Bade et al. |
| 2013/0305469 A1 * | 11/2013 | Rodriguez Sanjuan .................... A61B 1/122 |
| | | 15/104.05 |
| 2013/0322109 A1 | 12/2013 | Weiger |
| 2014/0066711 A1 | 3/2014 | Farin et al. |
| 2015/0080933 A1 | 3/2015 | Igov |
| 2015/0157311 A1 | 6/2015 | Shah |
| 2017/0281915 A1 | 10/2017 | Jalgaonkar et al. |
| 2017/0319047 A1 | 11/2017 | Poulsen et al. |

FOREIGN PATENT DOCUMENTS

| | | |
|---|---|---|
| EP | 1210904 A2 | 6/2002 |
| EP | 1323373 A2 | 7/2003 |
| EP | 2111782 A2 | 10/2009 |
| WO | 2015029040 A1 | 3/2015 |

\* cited by examiner

ENDOSCOPE AND CLEANING INSTRUMENT FOR AN ENDOSCOPE

CROSS REFERENCE TO RELATED APPLICATIONS

This application claims the benefit of priority under 35 U.S.C. § 119 of German Application 10 2016 109 066.2, filed May 17, 2016, the entire contents of which are incorporated herein by reference. This application is a divisional application of U.S. patent application Ser. No. 15/596,835, filed May 16, 2017, the entire contents of which are incorporated herein by reference.

TECHNICAL FIELD

The present invention relates to cleaning the light admission face at the distal end of an endoscope in situ, in particular to an endoscope and a cleaning instrument that facilitate such cleaning.

TECHNICAL BACKGROUND

During microinvasive procedures, there is a possibility of solid and liquid deposits gathering at the outer surface of an endoscope and therefore also at the light admission face at the distal end of the endoscope. These deposits may be caused by unwanted direct contact with a tissue surface, by blood or another bodily fluid, for example emerging at a wound, or by small tissue particles which are released and swirl around during the procedure. Moreover, moisture from the generally almost saturated atmosphere may condense at the light admission face of the endoscope.

Deposits at a light admission face of an endoscope may cause shading, scattering, refraction or diffraction of light and, consequently, a considerable deterioration of the image quality. Moreover, deposits at a light exit face, through which illumination light is intended to emerge at the distal end of an endoscope, adversely affect the image quality in general, since they reduce the intensity of the illumination light in the area to be observed, filter the illumination light and change the spectrum thereof. Moreover, deposits at a boundary area between a light exit face and a light admission face can cause direct coupling of illumination light into the observation beam path.

If no other precautions are taken in terms of equipment, a soiled endoscope has to be pulled out during the microsurgical procedure, cleaned and then inserted again. This takes up time and interrupts the flow of the microsurgical procedure. Moreover, an interruption of the microsurgical procedure, or of its visual monitoring, may pose a considerable risk to the patient in certain phases. In addition, the light admission face of the endoscope may cool during the cleaning outside of the body, as a result of which there is an increased risk of subsequent condensation of moisture. If an endoscope is held by a retainer arm or robotic arm, its cleaning is still more complicated.

EP 1 210 904 A2, EP 1 323 373 A2, U.S. Pat. Nos. 5,207,213, 5,392,766 and EP 2 111 782 A2 describe various measures by which the light exit face and light admission face at the distal end of an endoscope are cleaned in situ. These measures require their own installation space. As a result, the cross section of the endoscope shaft and/or the cross section of the lumen of a trocar tube is enlarged.

EP 0 434 793 B1 describes an endoscope with a video unit 1 arranged at the distal end. The video unit 1 is arranged pivotably and, during the insertion of the endoscope through a trocar tube within the contour of the endoscope, and during a microinvasive and/or minimally invasive procedure, can be arranged partially or completely outside the contour of the endoscope (FIGS. 1a, 1b, 1e, 6c, 6b, 6a). Moreover, an endoscope is described in which a video unit 1 is movable longitudinally inside a main channel 4 of a shaft 2 of the endoscope (paragraph [0075]; FIGS. 8a and 8b). When the video unit 1, at the operating site, is pushed distally out of the main channel 4 of the shaft 2 of the endoscope, it can free a part of the channel cross section (ibid).

Similar endoscopes are described in WO 2015/029040 and CH 698 893 B1.

US 2009/0231419 A1 describes a "main endoscope" 10 with a "longitudinal channel" 22 (paragraphs [0048] and [0051]; FIG. 3). A small endoscope ("minor endoscope") 20 with a further imaging device 42 is arranged in the longitudinal channel 22 (ibid). The small endoscope 20 has a flexible portion ("flexible link") 44 with a reduced cross section (paragraphs [0057] and [0076]; FIG. 3).

U.S. Pat. No. 6,387,043 B1 describes an endoscope which is designed as a trocar ("penetrating member") 12 with a cutting and optically transparent distal end 22 (column 4, lines 54 to 67; FIG. 3). In FIG. 3, an elongate tubular body 18 is shown with a smaller cross section than the distal end 22 and the proximal end 24.

U.S. Pat. No. 4,867,138 describes a rigid electronic endoscope 1 which can be arranged in a sheath 2 (column 3, lines 52 to 54; FIG. 1). The endoscope 1 has a tip 31 with a greater diameter, and a proximally adjoining part 32 with a "smaller diameter" (FIGS. 1 and 2). The cross section of the part 32 with a "smaller diameter" can be semi-circular with a straight edge portion (FIG. 4) or with recesses 61 (FIG. 5) or with protruding edges 62 (FIG. 6) or elliptical (FIG. 7; in fact with circular-arc-shaped and straight edge portions) or meniscus-shaped (FIG. 8) (column 6, lines 10 to 68).

U.S. Pat. No. 5,514,084 describes a retractable wiper for cleaning an endoscopic surgical instrument. The endoscopic surgical instrument and the retractable wiper are inserted through two different openings (FIG. 1).

Movable parts of an endoscope, in particular parts that are pivotable or displaceable relative to each other, reduce the mechanical robustness and very much increase the risk of damage. Moreover, the manufacture of the endoscope and also its cleaning are considerably more difficult.

SUMMARY

It is an object of the present invention to make available an improved endoscope, an improved cleaning instrument and an improved endoscopy system.

An endoscope comprises an endoscope shaft, with a distal shaft portion and a central shaft portion and a light admission face at the distal shaft portion, wherein the cross section of the central shaft portion is smaller than the cross section of the distal shaft portion.

An endoscope comprises an endoscope shaft, with a distal shaft portion, a central shaft portion and a proximal shaft portion, and a light admission face at the distal shaft portion, wherein the cross section of the central shaft portion is smaller than the cross section of the distal shaft portion and smaller than the cross section of the proximal shaft portion.

The endoscope is provided and designed in particular for microinvasive or other medical uses and/or for non-medical technical uses. The endoscope is in particular a video endoscope, which has at least one camera or at least one objective and at least one image sensor in the distal shaft portion. The image sensor converts an image generated by the objective at its surface into an image signal, which can be transmitted as analog or digital signal to the proximal end of the endoscope via a signal line in the central shaft portion.

The endoscope shaft is in particular substantially rigid and straight in sections. Alternatively, the endoscope shaft can be curved or flexible in sections or completely. Some of the features, properties and functions set out below may seem to be most easily and most obviously applicable to an endoscope with a rigid and straight endoscope shaft, but they can also be carried over in obvious manner to a curved or curvable endoscope shaft.

The distal shaft portion and the central shaft portion are each in particular substantially cylindrical with circular or other cross sections. Cylinders are not only circular cylinders, but general cylinders in the mathematical sense, i.e. bodies that are formed by moving a random base area along a straight line (cylinder axis). Departing from an ideal cylinder shape, the distal shaft portion and the central shaft portion can each in particular comprise grooves, webs or other facilities for guiding or holding an instrument or for form-fit definition of a predetermined position of an instrument, as are described below.

The central shaft portion, particularly if it contains only one or more lines for transmitting electrical or optical energy and an image signal, can have a substantially smaller cross section than the distal shaft portion.

The larger cross section of the distal shaft portion, optionally with camera or objective and image sensor, defines the cross section of the lumen of a trocar tube which is needed to be able to insert the distal shaft portion of the endoscope through the trocar tube into a body cavity. When the endoscope is inserted completely into the trocar tube and the distal shaft portion has completely passed through the trocar tube, the smaller cross section of the central shaft portion facilitates the ability of one or more further instruments to be guided through the same trocar tube parallel to the central shaft portion and past the latter. This may be possible with a conventional trocar tube and requires no mobility whatsoever of the distal shaft portion relative to the central shaft portion or relative to another component of the endoscope.

Examples of instruments that can be guided through the same trocar tube, parallel to the central shaft portion and past the latter, are a cleaning instrument for cleaning or drying the light admission face at the distal shaft portion of the endoscope; forceps, grippers and scissors for gripping, holding, squeezing, punching, cutting or other manipulation of tissue; a light guide for transmitting illumination light for improved and/or structured illumination of an object to be observed; a further or additional endoscope which can, for example, facilitate image capture in the near, mid or far infrared, the visible or the ultraviolet wavelength range; a probe for transmitting and applying laser light or other light of high power density or of electrical power for cutting and/or coagulating or otherwise changing tissue (in particular laser therapy, high-frequency surgery, electro-cauterization, photo-dynamic therapy); a tissue diagnosis probe, for example based on optical coherence tomography (OCT), confocal microscopy, spectroscopy, ultrasound; an optical projection system for (two-dimensional and/or three-dimensional) measurement of an object or of a cavity; a balloon applicator for dilation or enlargement or extension of a vessel or of another cavity.

In an endoscope as described here, the distal shaft portion is in particular rigidly connected to the central shaft portion.

Particularly in comparison with what is disclosed in EP 0 434 793 B1, the omission of hinges or of other forms of mobility of the distal shaft portion relative to the central shaft portion, or to any other part of the endoscope, can considerably reduce the manufacturing costs and considerably increase the mechanical robustness.

In an endoscope as described here, the distal shaft portion is in particular laterally offset with respect to the central shaft portion.

A lateral offset of the distal shaft portion relative to the central shaft portion, i.e. an offset of the distal shaft portion relative to the central shaft portion in a direction orthogonal to the longitudinal axes of the distal shaft portion, has in particular the effect that the distal shaft portion does not protrude laterally to the same extent in all directions with respect to the central shaft portion.

The longitudinal axis of a straight shaft portion is the straight line on which the center points of circular cross sections of the shaft portion or the area centers of gravity of non-circular cross sections of the shaft portion lie. In the case of a curved central shaft portion, references to the longitudinal axis of the central shaft portion are references to the straight line at which the curve, on which the center points or area centroids of the cross sections of the central shaft portion lie, asymptotically approaches the distal end of the central shaft portion.

In an endoscope as described here, in relation to a projection in a direction parallel to the longitudinal axis of the central shaft portion, the cross section of the central shaft portion is in particular arranged at the edge of the cross section of the distal shaft portion.

Thus, the distal shaft portion does not in particular protrude in a lateral direction (i.e. orthogonally with respect to the longitudinal axis of the central shaft portion). This can make it easier for an instrument to be guided past the endoscope shaft arranged in a lumen of a trocar tube.

In an endoscope as described here, the area of the cross section of the central shaft portion is in particular not more than two thirds or not more than a half or not more than a third or not more than a quarter of the area of the cross section of the distal shaft portion.

The area of a cross section signifies the area content of the surface enclosed by the outer contour of the cross section. The cross section of the central shaft portion can then in particular be much smaller than the cross section of the distal shaft portion if the central shaft portion only has one or more lines for transmitting electrical and/or optical power and control signals and image signals. The smaller the cross section of the central shaft portion, the greater the fraction of the cross section of the lumen of a trocar tube, into which the endoscope shaft is inserted, that remains for the insertion of one or more further instruments.

In an endoscope as described here, the edge of the cross section of the distal shaft portion is in particular circular and has a first radius, wherein the edge of the cross section of the central shaft portion is circular and has a second radius, which is smaller than the first radius.

The second radius is in particular approximately half (30% to 70% or 40% to 60%) of the first radius.

Circular cross sections can be produced easily and cost-effectively from tubular semi-finished products with circular cross sections, and they have a good ratio between mass and mechanical stiffness and robustness.

In an endoscope as described here, the edge of the cross section of the distal shaft portion is in particular circular and has a first radius, wherein the edge of the cross section of the central shaft portion has a circular-arc-shaped edge portion with a second radius, which is equal to the first radius or smaller than the first radius.

In an endoscope as described here, the edge of the cross section of the distal shaft portion is in particular circular and has a first radius, wherein the edge of the cross section of the central shaft portion has two circular-arc-shaped edge portions, wherein the radii of the circular-arc-shaped edge portions are each equal to the first radius or smaller than the first radius.

In an endoscope as described here, the edge of the cross section of the distal shaft portion is in particular circular and has a first radius, wherein the edge of the cross section of the central shaft portion has two circular-arc-shaped edge portions, wherein the radii of the circular-arc-shaped edge portions are each equal to the first radius or smaller than the first radius, and wherein the center points of the circular-arc-shaped edge portions are spaced apart from each other.

In particular, the center point of the first circular-arc-shaped edge portion is arranged between the second circular-arc-shaped edge portion and the center point of the second circular-arc-shaped edge portion, and the center point of the second circular-arc-shaped edge portion is arranged between the first circular-arc-shaped edge portion and the center point of the first circular-arc-shaped edge portion.

In particular, a cross section of the central shaft portion, of which the edge is formed from two circular-arc-shaped edge portions or substantially from two circular-arc-shaped edge portions whose radii are equal to the first radius, can facilitate a particularly efficient utilization of the cross section of the tube of a trocar. In particular, the ratio between the installation space available inside the central shaft portion and the mechanical stiffness of the central shaft portion, on the one hand, and the cross section remaining inside the lumen of the trocar tube for one or more further instruments, is particularly expedient.

In an endoscope as described here, the proximal shaft portion is in particular provided for insertion into the lumen of a tube.

In an endoscope as described here, the edge of the cross section of the proximal shaft portion is in particular circular.

In an endoscope as described here, the cross section of the proximal shaft portion corresponds in particular to the cross section of the distal shaft portion.

The proximal shaft portion can partially or completely close the lumen of a trocar tube into which the endoscope shaft is fully inserted. If the cross sections of the proximal shaft portion and of the distal shaft portion correspond to each other, the proximal shaft portion and the distal shaft portion can be provided, designed and in particular optimized for a use with a predetermined trocar tube. The cross section of the proximal shaft portion and the cross section of the distal shaft portion are in particular each chosen such that the distal shaft portion can be guided with low friction through the lumen of a predetermined trocar tube, for example a standard trocar tube, and the proximal shaft portion can be inserted with little play and little friction into the lumen of the same trocar tube.

In an endoscope as described here, in particular in relation to a projection in a direction parallel to the longitudinal axis of the central shaft portion, the cross section of the central shaft portion is arranged at the edge of the cross section of the proximal shaft portion.

When the proximal shaft portion is inserted in the intended manner into the lumen of a predetermined trocar tube, and in particular adopts a defined position therein with form-fit engagement, except for play, the central shaft portion lies at the inner wall of the trocar tube or is arranged near this and parallel to this. In this way, the largest possible part of the lumen of the trocar tube can remain for one or more other instruments.

In an endoscope as described here, the cross section of the distal shaft portion is in particular laterally offset in a first direction with respect to the cross section of the central shaft portion, wherein the cross section of the proximal shaft portion is laterally offset in a second direction with respect to the cross section of the central shaft portion, wherein the first direction and the second direction are counter to each other or different than each other.

In an endoscope as described here, in particular in relation to a projection in a direction parallel to the longitudinal axis of the central shaft portion, the cross section of the proximal shaft portion and the cross section of the distal shaft portion protrude in different directions with respect to the cross section of the central shaft portion.

In an endoscope as described here, in particular in relation to a projection in a direction parallel to the longitudinal axis of the central shaft portion, the cross section of the proximal shaft portion and the cross section of the distal shaft portion protrude in opposite directions with respect to the cross section of the central shaft portion.

The cross section of the proximal shaft portion and the cross section of the distal shaft portion protrude in particular in opposite directions with respect to the cross section of the central shaft portion. In the case of a straight endoscope shaft, a straight instrument guided past the central shaft portion can also be guided past the distal shaft portion.

In an endoscope as described here, the central shaft portion merges in particular at one side smoothly into the distal shaft portion and merges at an opposite side smoothly into the proximal shaft portion.

A smooth transition at one side is in particular a stepless transition, in which the surfaces of both adjoining shaft portions are flush at this side.

In an endoscope as described here, in relation to a projection in a direction parallel to the longitudinal axis of the central shaft portion, the cross section of the central shaft portion is arranged in particular at a portion of the edge of the cross section of the proximal shaft portion and at an opposite portion of the edge of the cross section of the distal shaft portion.

In an endoscope as described here, the cross section of the distal shaft portion merges in particular continuously into the cross section of the central shaft portion at the transition between the distal shaft portion and the central shaft portion, wherein the cross section of the central shaft portion merges continuously into the cross section of the proximal shaft portion at the transition between the central shaft portion and the proximal shaft portion.

A continuous transition from one cross section to another cross section is in particular a transition without or substantially without a step. The transition is in particular designed such that the transition cannot catch at an edge of the trocar tube or be impeded by form-fit engagement, neither during insertion into a trocar tube nor during removal from a trocar tube.

An endoscope as described here moreover comprises in particular a working channel for receiving an instrument in the proximal shaft portion, wherein a distal outlet opening of the working channel is arranged beside the proximal end of the central shaft portion.

The working channel can facilitate the guiding of an instrument through the proximal shaft portion. An instrument guided through the working channel and emerging from the distal outlet opening of the working channel can extend past the central shaft portion as far as the distal shaft portion and optionally beyond this. The endoscope can have a plurality of working channels, each for receiving one or more instruments in the proximal shaft portion.

In an endoscope as described here, the longitudinal axis of the distal end of the working channel is in particular parallel to the longitudinal axis of the proximal end of the central shaft portion.

In an endoscope as described here, the longitudinal axis of the working channel is in particular parallel to the longitudinal axis of the central shaft portion.

An endoscope as described here moreover comprises in particular a sealing facility for closing the working channel in a fluid-tight manner or for reducing the cross section of the working channel when no instrument is arranged in the working channel.

The sealing facility can prevent or reduce an escape of insufflation gas through the working channel.

In an endoscope as described here, the cross section of the working channel in the proximal shaft portion is in particular not circular.

In an endoscope as described here, the cross section of the working channel fills the cross section of the proximal shaft portion in particular substantially, less the cross section of the central shaft portion.

The cross section of the working channel fills the cross section of the proximal shaft portion substantially, less the cross section of the central shaft portion, in particular when the sum of the area of the cross section of the working channel and the area of the cross section of the central shaft portion amounts to at least half or at least two thirds or at least three quarters or at least four fifths or at least nine tenths of the area of the cross section of the proximal shaft portion.

An endoscope as described here moreover comprises in particular a guiding mechanism for guiding an instrument at the central shaft portion.

The guiding mechanism can moreover be provided and designed to guide an instrument at the distal shaft portion. The guiding mechanism comprises, for example, one or more longitudinal grooves or longitudinal webs for guiding an instrument with form-fit engagement. Alternatively or in addition, the guiding mechanism can comprise one or more paramagnetic or ferromagnetic areas for the magnetic guiding of an instrument at the central shaft portion and/or at the distal shaft portion.

The guiding mechanism can define a position of an instrument relative to the endoscope shaft in one or two directions orthogonal to the longitudinal axis of the endoscope shaft and can do so by form-fit engagement, magnetically or in some other way. Alternatively or in addition, the guiding mechanism can define a position of an instrument relative to the endoscope shaft in a direction parallel to the longitudinal axis of the endoscope shaft, for example by a mechanical abutment or by means of a latch facility or magnetically.

A cleaning instrument for cleaning or drying a light admission face at a distal shaft portion of an endoscope comprises an instrument shaft and a tool at the distal end of the instrument shaft for cleaning or drying the light admission face at the distal shaft portion of the endoscope, wherein the instrument shaft is provided and designed for arrangement beside an endoscope shaft of the endoscope.

A cleaning instrument for cleaning or drying the light admission face at the distal shaft portion of an endoscope, as described here, comprises an instrument shaft and a tool at the distal end of the instrument shaft for cleaning or drying the light admission face at the distal shaft portion of the endoscope, wherein the instrument shaft is provided and designed for arrangement beside the endoscope shaft of the endoscope.

The instrument shaft is in particular longer than the endoscope shaft of the endoscope for which the cleaning instrument is provided. The instrument shaft is in particular not provided and designed for arrangement in a working channel that extends along an entire endoscope shaft as far as the distal end of the endoscope. The instrument shaft is in particular not provided to receive an endoscope shaft. The instrument shaft is in particular provided and designed for arrangement beside the central shaft portion and optionally also beside the distal shaft portion of an endoscope.

In a cleaning instrument as described here, the cross section of the instrument shaft is in particular adapted to the cross section of the central shaft portion of the endoscope such that the total cross section of a parallel arrangement of the instrument shaft and of the central shaft portion of the endoscope is not greater than the cross section of the distal shaft portion of the endoscope.

The parallel arrangement of the instrument shaft and of the central shaft portion of the endoscope is an arrangement in which the longitudinal axis of the instrument shaft is parallel to the longitudinal axis of the central shaft portion of the endoscope. The parallel arrangement of the instrument shaft and of the central shaft portion is in particular an arrangement in which the instrument shaft bears at the central shaft portion of the endoscope.

The total cross section of the parallel arrangement is in particular smaller than the cross section of the distal shaft portion of the endoscope. If the endoscope, proximally of the central shaft portion, has a proximal shaft portion with a cross section greater than the cross section of the central shaft portion, the total cross section of the parallel arrangement of the instrument shaft and of the central shaft portion of the endoscope is in particular also smaller or not greater than the cross section of the proximal shaft portion of the endoscope.

A cleaning instrument as described here moreover comprises in particular a fluid channel in the instrument shaft, wherein the tool comprises a nozzle, which is connected to the distal end of the fluid channel, wherein the nozzle is provided and designed to convey a fluid to the light admission face of the endoscope.

The fluid channel and the nozzle can facilitate the generation of a flow, in particular of a sharp jet, of insufflation gas for drying the light admission face or for removing a liquid or solid deposit at the light admission face. Alternatively or in addition, the fluid channel and the nozzle can facilitate the generation of a jet of saline solution or of another flushing liquid, directed to the light admission face, in order to remove a liquid or solid deposit at the light admission face.

In a cleaning instrument as described here, the nozzle is in particular provided and designed to form a stream of fluid at the light admission face of the endoscope, in order at least to remove a deposit at the light admission face or also to prevent the formation of a deposit at the light admission face.

A continuous stream of gas having a sufficient flow velocity may be suitable for picking up and carrying away particles or droplets of a liquid before they are able to reach the light admission face.

A cleaning instrument as described here moreover comprises in particular a guiding mechanism for guiding the cleaning instrument at a shaft of the endoscope.

The guiding mechanism comprises in particular a longitudinal groove, a longitudinal web, a paramagnetic or ferromagnetic area for guiding the cleaning instrument at an endoscope shaft of the endoscope by form-fit engagement or magnetically. The guiding mechanism is in particular provided and designed for interaction with a corresponding guiding mechanism at the endoscope shaft. The guiding mechanism can be punctiform or linear and can extend along the entire instrument shaft or can be arranged only at the distal end of the instrument shaft or at the tool.

An external action, the recoil of an emerging fluid or and the direct mechanical interaction of the tool with the light admission face or with deposits on the light admission face can generate a force that causes a deformation of the cleaning instrument and a movement of the tool away from its intended position. Despite the action of such a force, the guiding mechanism can facilitate a defined position of the tool relative to the endoscope shaft.

In a cleaning instrument as described here, the tool comprises in particular a wiping facility for wiping deposits at the light admission face of the endoscope.

The wiping facility comprises in particular an elastic wiper blade or a doctor made of silicone, rubber or another elastic material for wiping dirt, moisture or other solid or liquid deposits away from the light admission face of the endoscope. The wiping facility can be provided and designed to be moved relative to the light admission face of the endoscope by a rotation movement of the instrument shaft, and with it of the tool, by a movement of the instrument shaft parallel to its longitudinal axis, or in another way.

In a cleaning instrument as described here, the tool has in particular a hinge that facilitates placement of a wiping lip onto the light admission face of the endoscope.

The hinge can be a flexure bearing. In addition to the hinge, an elastic facility can be provided which can press or place the wiping lip onto the light admission face of the endoscope.

The hinge can facilitate a movement of the tool between an insertion position and a working position. In the insertion position of the tool, the cleaning instrument can be guided through a working channel in an endoscope and can be guided beside a central shaft portion of the endoscope through the lumen of a trocar tube. In the working position, a light admission face of the endoscope can be cleaned. Moreover, in the case of an inclined or curved light admission face, the hinge can make it easier for the tool to follow the light admission face.

In a cleaning instrument as described here, the tool in particular comprises a wiping lip, which is arranged nonparallel to the longitudinal axis of the instrument shaft and which is provided to wipe deposits away from the light admission face of the endoscope during a movement of the cleaning instrument in a direction parallel to the longitudinal axis of the instrument shaft relative to the endoscope.

The wiping lip is in particular arranged orthogonally or substantially orthogonally to the longitudinal axis of the instrument shaft. The wiping lip is arranged substantially orthogonally to the longitudinal axis of the instrument shaft when the angle between the wiping lip and the longitudinal axis of the instrument shaft is at least 60 degrees or at least 70 degrees or at least 80 degrees. Particularly in combination with a hinge that facilitates a pivoting of the tool or at least of the wiping lip about a pivot axis orthogonal or substantially orthogonal to the longitudinal axis of the instrument shaft, the wiping lip can be guided across the light admission face by mere movement of the instrument shaft parallel to its longitudinal axis.

In a cleaning instrument as described here, the wiping lip is in particular pivotable about a pivot axis in order to wipe deposits away from the light admission face of the endoscope.

The pivot axis is in particular parallel to the longitudinal axis of the instrument shaft. The pivoting movement of the wiping lip can be generated by a drive shaft in the instrument shaft or by rotation of the instrument shaft about its longitudinal axis. In this case, the wiping lip can clean the light admission face in a manner similar to a wiper blade of a windscreen of a vehicle.

An endoscopy system comprises an endoscope, as described here, and a cleaning instrument, as described here.

An endoscopy system comprises an endoscope, as described here, and a trocar tube with a lumen for receiving the endoscope shaft of the endoscope, wherein the endoscope shaft of the endoscope and the trocar tube are designed such that the distal shaft portion of the endoscope can be guided completely through the trocar tube.

In particular, the cross section of the distal shaft portion of the endoscope shaft and the cross section of the lumen of the trocar tube are configured such that the distal shaft portion of the endoscope can be guided with little friction all the way through the trocar tube.

The trocar tube can be straight or curved. If the endoscope has a curved shaft, the trocar tube has in particular a corresponding curvature.

In an endoscopy system as described here, the trocar tube or a cylindrical portion of the lumen of the trocar tube is in particular not longer than the central shaft portion of the endoscope.

The trocar tube or a cylindrical portion of the lumen of the trocar tube is in particular shorter than the central shaft portion of the endoscope. If the trocar tube or a cylindrical portion of the lumen of the trocar tube is not longer than the central shaft portion of the endoscope, the endoscope shaft can be moved in a direction orthogonal to the longitudinal axis of the central shaft portion whenever only the central shaft portion is arranged in the trocar tube or in the cylindrical portion of the lumen of the trocar tube. This movement can be carried out between the guiding of the distal shaft portion through the trocar tube, or the cylindrical portion of the lumen of the trocar tube, and the insertion of a proximal shaft portion into the trocar tube.

In an endoscopy system as described here, the proximal shaft portion of the endoscope and the trocar tube are provided and designed such that the trocar tube receives the proximal shaft portion.

In particular, the proximal shaft portion of the endoscope and the trocar tube are designed such that the proximal shaft portion of the endoscope is guided in the trocar tube with little play and little friction.

An endoscopy system as described here moreover comprises in particular a cleaning instrument, as described here.

An endoscopy system as described here moreover comprises in particular a cleaning instrument, as described here, wherein the central shaft portion of the endoscope, the instrument shaft of the cleaning instrument and the trocar tube are provided and designed such that the cross section of the central shaft portion of the endoscope and the cross section of the instrument shaft of the cleaning instrument substantially fill the cross section of the lumen of the trocar tube.

The cross section of the central shaft portion of the endoscope and the cross section of the instrument shaft of the cleaning instrument substantially fill the cross section of the lumen of the trocar tube when the total cross section of the central shaft portion of the endoscope and of the instrument shaft of the cleaning instrument occupies at least half or at least two thirds or at least three quarters or at least four fifths or at least nine tenths of the area of the cross section of the lumen of the trocar tube.

In a method for preparing for the use of an endoscope, an endoscope is inserted into a trocar tube as far as a predetermined position, the endoscope is moved in the trocar tube in a direction orthogonal to the direction of insertion, and the endoscope is moved as far as a working position in the trocar tube.

The method can be carried out in particular with an endoscope and a trocar tube as are described here, or with an endoscope and a trocar tube having features, properties and functions as are described here. In particular, the method can be carried out with an endoscope which has a central shaft portion whose cross section is smaller than the cross section of a distal shaft portion. The predetermined position is in particular a position in which only the central shaft portion is arranged in the trocar tube or in a cylindrical portion of the lumen of the trocar tube. In the working position of the endoscope relative to the trocar tube, a proximal shaft portion of the endoscope is in particular inserted into the trocar tube.

In a method as described here, a cleaning instrument or another instrument can be guided past a shaft portion (in particular a central shaft portion) of the endoscope in the working position.

In an optional preceding step, the instrument can be guided through a working channel of the endoscope. The distal outlet opening of the working channel is in particular arranged beside the proximal end of the shaft portion that is arranged at the predetermined position in the trocar tube.

In an optional further step, a light admission face of the endoscope is cleaned with the instrument.

Embodiments are explained in more detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
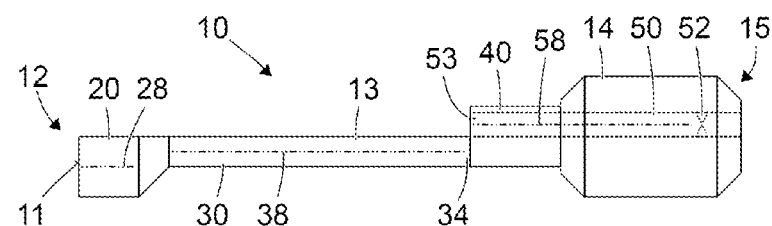
FIG. 1 is a schematic view of an endoscope.

Referring to the drawings, FIG. 1 shows a schematic view of an endoscope 10 with a light admission face 11 at the distal end 12 of the endoscope 10, an endoscope shaft 13 and a manipulation facility 14, which forms the proximal end 15 of the endoscope 10. The endoscope shaft 13 has several cylindrical or substantially cylindrical shaft portions 20, 30, 40. Each of the shaft portions 20, 30, 40 can have a circular cross section or another cross section. In the example shown, each shaft portion 20, 30, 40 has a circular cross section, i.e. the shaft portions 20, 30, 40 have the shape of circular cylinders.

The outer edge or the contour of the cross section of the distal shaft portion 20 is congruent or substantially congruent to the outer edge of the cross section of the proximal shaft portion 40, i.e. the distal shaft portion 20 and the proximal shaft portion 40 have the same diameter or the same radius. The central shaft portion 30 has a much smaller cross section with a much smaller diameter.

A camera or a combination of an objective and an image sensor can be arranged in the distal shaft portion 20. The image sensor converts an image generated by the objective into an analog or digital signal, which is transmitted to the proximal end 15 of the endoscope 10 by means of one or more signal lines in the endoscope shaft 13. Alternatively, the distal shaft portion 20 can have an objective for capturing an intermediate real image, which is transmitted to the proximal end of the endoscope 10 by means of a relay lens system in the endoscope shaft 13.

A device for changing the viewing direction of the endoscope can additionally be arranged in the distal shaft portion 20, for example a pivotable prism, at the surface of which total reflection takes place, or other pivotable reflecting surfaces.

Beside the light admission face 11, one or more light exit faces can additionally be arranged, through which illumination light emerges for illuminating an object that is to be viewed. Cleaning of a light admission face, as described below, can also entail the cleaning of one or more adjacent light exit faces.

The distal shaft portion 20 is connected to the central shaft portion 30 in a mechanically rigid manner, in such a way that the longitudinal axis 28 of the distal shaft portion 20 is parallel to the longitudinal axis 38 of the central shaft portion 30, and such that the longitudinal axis 28 of the distal shaft portion 20 is laterally offset with respect to the longitudinal axis 38 of the central shaft portion 30. In a projection parallel to the longitudinal axes 28, 38 of the distal shaft portion 20 and of the central shaft portion 30, the distal shaft portion 20 protrudes in one direction (downward in FIG. 1), whereas at the opposite side (upward in FIG. 1) the contour of the distal shaft portion 20 is flush with the contour of the central shaft portion 30.

In the example shown, a conical or substantially conical transition area is provided between the distal shaft portion 20 and the central shaft portion 30. Alternatively, an abrupt or step-shaped transition can be provided between the distal shaft portion 20 and the central shaft portion 30.

The proximal shaft portion 40 is laterally offset with respect to the central shaft portion 30. In a projection parallel to the longitudinal axis 38 of the central shaft portion 30 and to the longitudinal axis (not shown in FIG. 1) of the proximal shaft portion 40, the contour of the central shaft portion merges smoothly at one side (downward in FIG. 1) into the contour of the proximal shaft portion 40, whereas the contour of the proximal shaft portion at an opposite side (upward in FIG. 1) protrudes with respect to the contour of the central shaft portion 30.

In the example shown, the transition between the central shaft portion 30 and the proximal shaft portion 40 is step-shaped. The cross section of the endoscope shaft 13 thus changes abruptly from the distal end (on the left in FIG. 1) to the proximal end (on the right in FIG. 1) without a transition area. Alternatively, a continuous or smooth transition can be provided between the central shaft portion 30 and the proximal shaft portion 40.

In the proximal shaft portion 40 and in the manipulation facility 14 of the endoscope 10, a working channel 50 is provided, of which the contours are indicated in FIG. 1 by broken lines. The working channel 50 is provided and designed to receive an instrument, for example a cleaning instrument for cleaning the light admission face 11 at the distal end 12 of the endoscope 10.

A sealing facility 52 is arranged in the working channel 50. The sealing facility 52 is provided and designed to close and seal off, in a fluid-tight manner, an annular gap remaining between the inner surface of the working channel 50 and an outer surface of an instrument inserted into the working channel 50. Alternatively or in addition, the sealing facility 52 is provided and designed to close the working channel 50 in a fluid-tight manner or at least to considerably reduce the cross section thereof, when no instrument is inserted in the working channel 50.

A distal outlet opening 53 of the working channel 50 is arranged beside the proximal end 34 of the central shaft portion 30. The longitudinal axis 58 of the working channel 50 is parallel to the longitudinal axis 38 of the central shaft portion 30 and parallel to the longitudinal axis (not shown in FIG. 1) of the proximal shaft portion 40.

Figure 2:
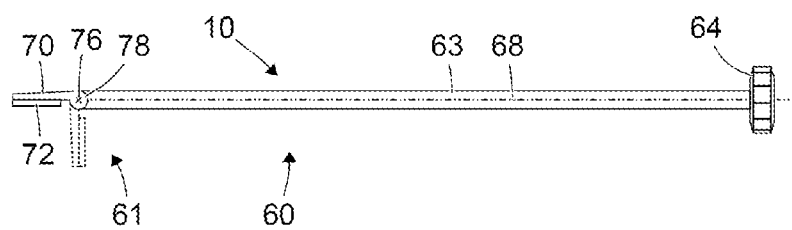
FIG. 2 is a schematic view of a cleaning instrument.

FIG. 2 shows a schematic view of a cleaning instrument 60 for cleaning a light admission face of an endoscope, in particular the light admission face 11 of the endoscope 10 shown in FIG. 1. The cleaning instrument 60 comprises a distal end 61, an instrument shaft 63 and a manipulation facility in the form of a wheel 64, which forms the proximal end of the cleaning instrument 60. The wheel 64 is provided in particular to manually rotate the cleaning instrument about the longitudinal axis 68 of the instrument shaft 63.

The distal end 61 of the cleaning instrument 60 is formed by a cleaning tool 70 with a wiping lip 72 for wiping away liquid or solid deposits at a light admission face of an endoscope. The cleaning tool 70 is connected to the instrument shaft 63 in an articulated manner by a hinge 76. The hinge 63 facilitates pivoting of the cleaning tool 70 about a pivot axis 78 orthogonal to the longitudinal axis 68 of the instrument shaft 63 and orthogonal to the drawing plane of FIG. 2.

In FIG. 2, the cleaning tool 70 is indicated in an insertion position by solid lines and in a working or cleaning position by broken lines. The cleaning instrument 60 comprises an elastic facility or another facility that moves the cleaning tool 70 to the working or cleaning position indicated by broken lines in FIG. 2. Counter to the elastic force of the elastic facility, the cleaning tool 70 can be moved to the insertion position shown by solid lines in FIG. 2.

Figure 3:
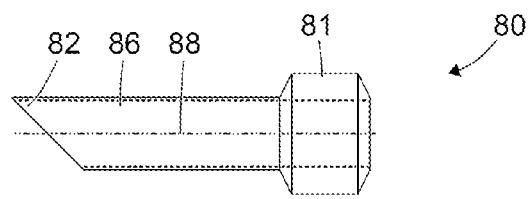
FIG. 3 is a schematic view of a trocar tube.

FIG. 3 shows a schematic view of a trocar tube 80 with a proximal end 81 and a distal end 82. The proximal end 81 of the trocar tube 80 can be formed by a manipulation facility indicated in FIG. 3. A lumen 86 extends from the proximal end 81 to the distal end 82 of the trocar tube. In the example shown, the lumen 86 has the shape of a cylinder, in particular a circular cylinder, all the way from the proximal end 81 to the distal end 82. The contours of the lumen 86 are not visible in FIG. 3 and are therefore indicated only by broken lines.

Figure 4:
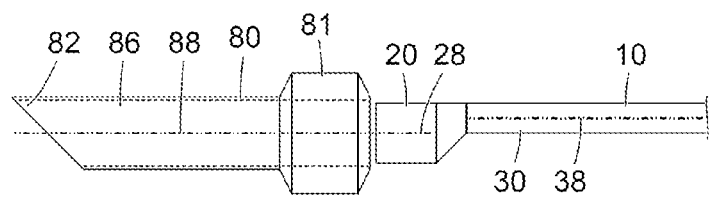
FIG. 4 is a schematic view of an endoscopy system composed of the endoscope from FIG. 1 and of the trocar tube from FIG. 3.

FIG. 4 shows a schematic view of an endoscopy system which comprises an endoscope 10 and a trocar tube 80, in particular the endoscope 10 shown in FIG. 1 and the trocar tube 80 shown in FIG. 3. Only the distal shaft portion 20 and a part of the central shaft portion 30 of the endoscope 10 are visible in FIG. 4. The distal shaft portion 20 is arranged near the proximal end 81 of the trocar tube 80 and is positioned and oriented relative to the lumen 86 in the trocar tube 80 in such a way that the distal shaft portion 20, with a movement of the entire endoscope 10 relative to the trocar tube 80, can be moved in the distal direction (to the left in FIG. 4) through the lumen 86 of the trocar tube 80.

Figure 5:
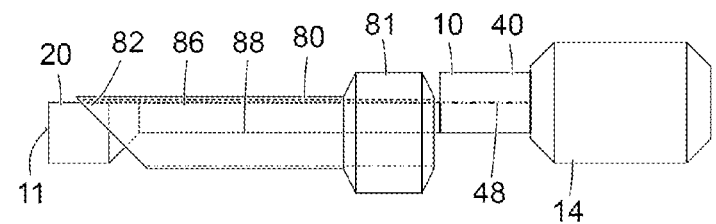
FIG. 5 is a further schematic view of the endoscopy system from FIG. 4.

FIG. 5 shows a further schematic view of the endoscopy system from FIG. 4. FIG. 5 shows a situation or configuration that arises when the endoscope 10, starting from the position shown in FIG. 4, is moved distally relative to the trocar tube 80 parallel to the longitudinal axis 88 of the trocar tube 80, parallel to the longitudinal axis 28 of the distal shaft portion 20, parallel to the longitudinal axis 38 of the central shaft portion 30 and parallel to the longitudinal axis 48 of the proximal shaft portion 40.

In the position of the endoscope 10 relative to the trocar tube 80 in FIG. 5, one side (the upper side in FIG. 5) of the central shaft portion 30 bears at the inner surface of the lumen 86 of the trocar tube 80 or is spaced slightly apart therefrom.

Figure 6:
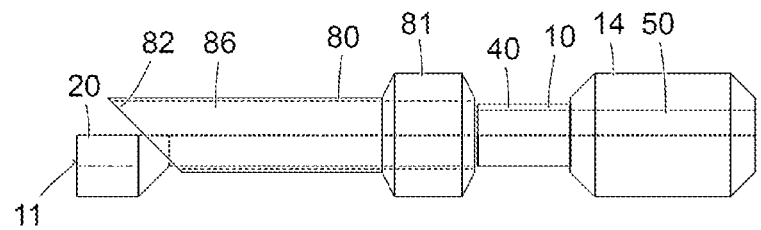
FIG. 6 is a further schematic view of the endoscopy system from FIGS. 4 and 5.

FIG. 6 shows a further schematic view of the endoscopy system from FIGS. 4 and 5. The situation shown in FIG. 6 arises when the endoscope 10, starting from the position shown in FIG. 5, is moved relative to the trocar tube in a direction orthogonal to the longitudinal axis 28 of the distal shaft portion 20, orthogonal to the longitudinal axis of the central shaft portion and orthogonal to the longitudinal axis 88 of the trocar tube 80, specifically from the top downward in the view in FIG. 6.

In the position of the endoscope 10 relative to the trocar tube 80 in FIG. 6, the central shaft portion 30 bears at an opposite side (the lower side in FIG. 6) compared to the situation shown in FIG. 5 on the inner surface of the lumen 86 of the trocar tube 80 or is spaced slightly apart therefrom.

Figure 7:
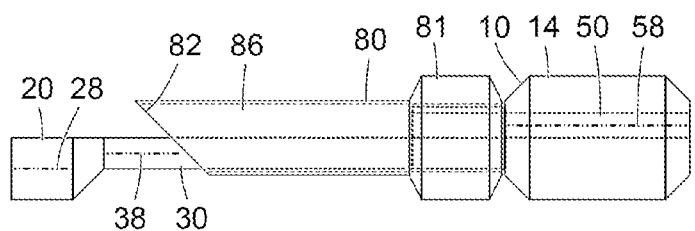
FIG. 7 is a further schematic view of the endoscopy system from FIGS. 4 to 6.

FIG. 7 show a further schematic view of the endoscopy system from FIGS. 4 to 6. The situation shown in FIG. 7 arises when the endoscope 10, starting from the position shown in FIG. 6, is moved further distally relative to the trocar tube 80 in a direction parallel to the longitudinal axis 28 of the distal shaft portion 20, parallel to the longitudinal axis 38 of the central shaft portion 30 and parallel to the longitudinal axis of the trocar tube 80. In doing this, the proximal shaft portion 40 is inserted into the lumen 86 of the trocar tube 80.

In the situation shown in FIG. 7, the proximal shaft portion 40 is inserted completely into a proximal area of the lumen 86 of the trocar tube 80. The manipulation facility 14 bears at the proximal end 81 of the trocar tube 80.

Figure 8:
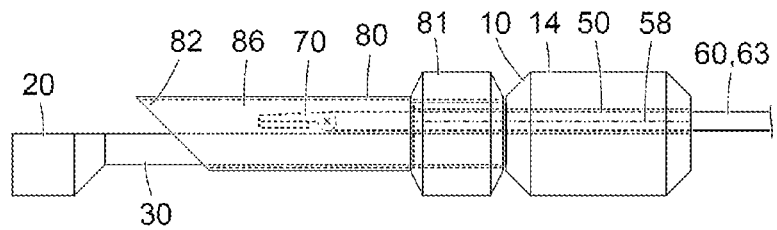
FIG. 8 is a schematic view of an endoscopy system composed of the endoscope from FIG. 1, the cleaning instrument from FIG. 2 and the trocar tube from FIG. 3.

FIG. 8 shows a schematic view of an endoscopy system which, like the endoscopy system shown in FIGS. 4 to 7, comprises an endoscope 10 and a trocar tube 80, in particular the endoscope 10 shown in FIG. 1 and the trocar tube 80 shown in FIG. 3. Furthermore, the endoscopy system shown in FIG. 8 comprises a cleaning instrument 60, in particular the cleaning instrument 60 shown in FIG. 2.

In the situation shown in FIG. 8, the cleaning tool 70 at the distal end of the cleaning instrument 60 adopts the insertion position (shown by solid lines in FIG. 2) relative to the instrument shaft 63. The cleaning tool 70 is inserted from the proximal end completely through the working channel 50 in the endoscope 10 into the lumen 86 in the trocar tube 80. The instrument shaft 63 of the cleaning instrument 60 is inserted partially into the working channel 50 of the endoscope 50 and partially into the lumen 86 of the trocar tube 80.

Figure 9:
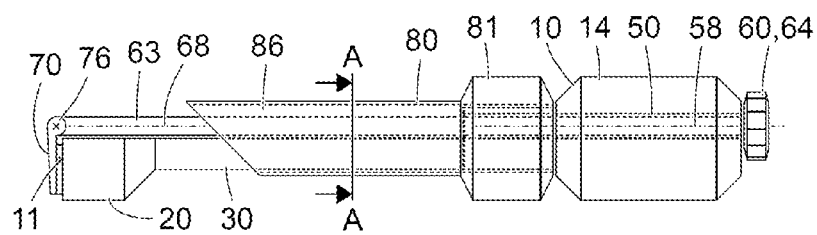
FIG. 9 is a further schematic view of the endoscopy system from FIG. 8.

FIG. 9 show a further schematic view of the endoscopy system from FIG. 8. The situation shown in FIG. 9 arises when the cleaning instrument 60, starting from the position shown in FIG. 8, is moved distally relative to the endoscope 10 and the trocar tube 80 parallel to the longitudinal axis 68 of the instrument shaft 63 and parallel to the longitudinal axis 58 of the working channel 50, as far as the working or cleaning position shown in FIG. 9.

The elastic restoring force (described with reference to FIG. 2) of an elastic facility (not shown in the figures) moves the cleaning tool to the cleaning position shown in FIG. 9, in which the wiping lip 72 bears at the light admission face 11 of the endoscope 10. The wheel 64 can be rotated manually about the longitudinal axis 68 of the instrument shaft 63. The instrument shaft 63 thus rotates together with the tool 70 about the longitudinal axis 68 of the instrument shaft 63, and the wiping lip 72 of the cleaning tool 70 is moved across the light admission face 11 of the endoscope 10. In this way, solid and liquid deposits at the light admission face 11 of the endoscope 10 and optionally at adjacent light exit faces can be wiped off or pushed aside, in order to facilitate capture of a sharp, high-contrast and bright image.

Figure 10:
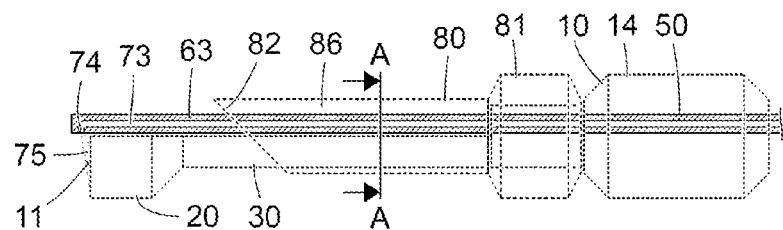
FIG. 10 is a schematic view of a further cleaning instrument.

FIG. 10 shows a schematic view of a further cleaning instrument 60 which is similar, in some features, properties and functions, to the cleaning instrument shown in FIGS. 2, 8 and 9. Features, properties and functions of the cleaning instrument 60 shown in FIG. 10 are in particular described below which differentiate it from the cleaning instrument shown in FIGS. 2, 8 and 9. In contrast to the views in FIGS. 1 to 9, the cleaning instrument 60 in FIG. 10 is shown in a longitudinal section. An endoscope 10 and a trocar tube 80, in particular the endoscope 10 shown in FIG. 1 and the trocar tube shown in FIG. 3, are indicated by broken lines. The cleaning instrument 60 can form an endoscopy system together with the endoscope 10 and/or with the trocar tube 80. The position of the cleaning instrument 60 indicated in FIG. 10 is the intended working or cleaning position relative to the endoscope 10.

The cleaning instrument 60 has a fluid channel 73 in the instrument shaft 63, which fluid channel 73 is connected to a nozzle 74 at the distal end of the cleaning instrument 60. A gas, a saline solution or another cleaning liquid or another cleaning fluid can be conveyed through the fluid channel 73 to the nozzle 74, emerge through the nozzle 74 and form a stream 75 of fluid. The nozzle 74 is arranged and designed such that the stream 75 of fluid strikes the light admission face 11 and carries off solid or liquid deposits at the light admission face 11. Alternatively or in addition, the nozzle 74 can be designed such that a stream 75 of gas formed by the nozzle 74 and moving along the light admission face 11 of the endoscope 10 suppresses the formation of solid or liquid deposits at the light admission face 11.

Figure 11:
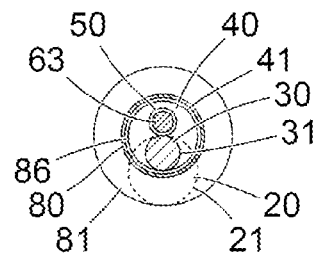
FIG. 11 is a schematic view of a cross section of the endoscopy system from FIGS. 8 and 9.

FIG. 11 shows a schematic view of a cross section through the endoscopy system shown in FIGS. 8 and 9, or through an endoscopy system with the cleaning instrument shown in FIG. 10, along the section plane A-A indicated in FIGS. 9 and 10.

The cross section of the central shaft portion 30 and the cross section of the instrument shaft 63 of the cleaning instrument 60 (cf. FIGS. 8 to 10) are each shown without inner structure. The distal shaft portion 20 of the endoscope 10 (cf. FIGS. 1 and 8 to 10) lies in front of the section plane A-A and is therefore not visible in FIG. 11. In order to visualize the position of the distal shaft portion 20 relative to the central shaft portion 30 and relative to the proximal shaft portion 40, the edge 21 of the cross section of the distal shaft portion 20 is indicated in FIG. 11 by a broken line. This corresponds to a projection in a direction parallel to the longitudinal axes 28, 38, 48, 58, 68, 88 (cf. FIGS. 1 to 5).

The edge 21 of the cross section of the distal shaft portion 20, the edge 31 of the cross section of the central shaft portion 30 and the edge 41 of the cross section of the proximal shaft portion 40 are each circular, while the cross section of the trocar tube 80 has the shape of a circular ring. The distal shaft portion 20, the central shaft portion 30 and the proximal shaft portion 40 are arranged relative to one another such that the cross section of the central shaft portion 30 lies at the edge of the cross section of the distal shaft portion 20 and at the edge 41 of the cross section of the proximal shaft portion 40. The cross sections of the distal shaft portion 20 and of the proximal shaft portion 40 are offset relative to the central shaft portion 30 such that the distal shaft portion 20 and the proximal shaft portion 40 protrude in opposite directions relative to the central shaft portion 30.

Figure 12:
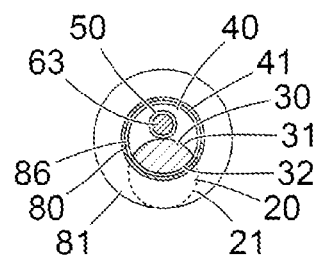
FIG. 12 is a schematic view of a cross section through a further endoscopy system.

FIG. 12 shows a schematic view of a cross section through a further endoscopy system which is similar, in some features, properties and functions, to the endoscopy systems shown in FIGS. 1 to 11. The section plane of FIG. 12 corresponds to the section plane A-A of FIG. 11. Features, properties and functions of the endoscopy system shown in FIG. 12 are in particular described below which differentiate it from the endoscopy systems shown in FIGS. 1 to 11.

The endoscopy system shown in FIG. 12 differs from the endoscopy systems shown in FIGS. 1 to 11 in particular in that the central shaft portion 30 of the endoscope does not have a circular cross section. Instead, the central shaft portion 30 has an edge which is formed by two edge portions 31, 32 that each have the shape of an arc of a circle. The circular-arc-shaped edge portions 31, 32 each have the same radius as the edge 21 of the cross section of the distal shaft portion 20 and the edge 41 of the cross section of the proximal shaft portion 40.

The distal shaft portion 20, the central shaft portion 30 and the proximal shaft portion 40 are arranged such that, in the projection shown in FIG. 12, the first circular-arc-shaped edge portion 31 of the cross section of the central shaft portion 30 overlaps the edge 21 of the distal shaft portion 20, and such that the second circular-arc-shaped edge portion 32 of the central shaft portion 30 overlaps the edge 41 of the proximal shaft portion 40. Thus, a part of the surface of the central shaft portion 30 is flush with a part of the surface of the distal shaft portion 20 and merges smoothly into the latter. Another part of the surface of the central shaft portion 30 is flush with a part of the surface of the proximal shaft portion 40 and merges smoothly into the latter.

Figure 13:
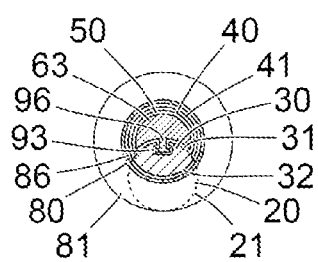
FIG. 13 is a schematic view of a cross section through a further endoscopy system.

FIG. 13 shows a schematic view of a cross section through a further endoscopy system which is similar, in some features, properties and functions, to the endoscopy systems shown in FIGS. 1 to 11 and in particular to the endoscopy system shown in FIG. 12. The section plane of FIG. 13 corresponds to the section plane A-A of FIG. 11 and to the section plane of FIG. 12. Features, properties and functions of the endoscopy system shown in FIG. 13 are described below which differentiate it from the endoscopy systems shown in FIGS. 1 to 12.

The endoscopy system shown in FIG. 13 differs from the endoscopy systems shown in FIGS. 1 to 12, and especially from the endoscopy system shown in FIG. 12, in that, among other things, the cross section of the working channel 50 in the proximal shaft portion 40 and the corresponding cross section of the instrument shaft 63 each have a crescent shape. The edges of the cross sections of the working channel 50 and of the instrument shaft 63 are each composed substantially of two circular-arc-shaped edge portions. The radius of one circular arc portion is slightly greater, and the radius of the other circular arc portion slightly smaller, than the radii of the edges or edge portions 21, 31, 32, 41 of the cross sections of the shaft portions 20, 30, 40. The cross section of the central shaft portion 30 and the cross section of the instrument shaft 63 together fill the cross section of the lumen 86 of the trocar tube 80 substantially, in particular except for a structurally required wall thickness of the proximal shaft portion 40.

The endoscopy system shown in FIG. 13 moreover differs from the endoscopy systems shown in the figures in that the instrument shaft 63 is guided with form-fit engagement at the central shaft portion 30 and optionally also at the distal shaft portion. For this purpose, the central shaft portion 30 has a groove 93 and the instrument shaft 63 has a web 96. The groove 93 and the web 96 have corresponding T-shaped cross sections. The web 96 engages in the groove 93. Form-fit engagement between the groove 93 and the web 96 suppresses a movement of the instrument shaft 63 relative to the central shaft portion 30 substantially or, except for unavoidable play, completely.

As an alternative to T-shaped cross sections, the groove 93 and the web 96 can have dovetail-shaped cross sections.

A distal end of the groove 93 and a distal end of the web 96 can form a mechanical stop, which by form-fit engagement defines a working or cleaning position (cf. FIGS. 9 and 10).

Figure 14:
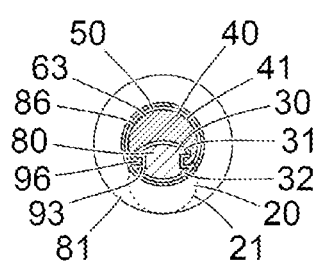
FIG. 14 is a schematic view of a cross section through a further endoscopy system.

FIG. 14 shows a schematic view of a cross section through a further endoscopy system which is similar, in some features, properties and functions, to the endoscopy systems shown in FIGS. 1 to 13. The section plane of FIG. 14 corresponds to the section planes of FIGS. 11 to 13. Features, properties and functions of the endoscopy system shown in FIG. 14 are in particular described below which differentiate it from the endoscopy systems shown in FIGS. 1 to 13.

The endoscopy system shown in FIG. 14 differs from the endoscopy systems shown in FIGS. 1 to 12, and in particular from the endoscopy system shown in FIG. 13, in that, among other things, the cross section of the central shaft portion 30 and the cross section of the instrument shaft 63 together fill the lumen 86 of the trocar tube 80 substantially completely. For this purpose, the proximal shaft portion 40 (cf. FIGS. 1 and 5 to 13) can be omitted. In this case, the endoscope is then guided with little play in the trocar tube 80 only if at the same time the instrument shaft 63 is inserted into the working channel 50 in the manipulation facility 14 of the endoscope 10 (cf. FIGS. 1 and 5 to 10) and at least partially into the lumen 86 of the trocar tube 80.

In contrast to the view in FIGS. 3 to 10, the lumen 86 of the trocar tube 80 can alternatively have a widened cross section near the proximal end 81, in order to receive a correspondingly larger proximal shaft portion 40.

The endoscopy system shown in FIG. 14 moreover differs from the endoscopy systems shown in FIGS. 1 to 13, and in particular from the endoscopy system shown in FIG. 13, in that a guiding of the instrument shaft 63 with form-fit engagement at the central shaft portion 30 of the endoscope is provided in another way. The central shaft portion 30 has a groove 93 at each of its two edges facing away from each other. An associated L-shaped web 96 at the instrument shaft 63 engages in each of the two grooves 93.

Figure 15:
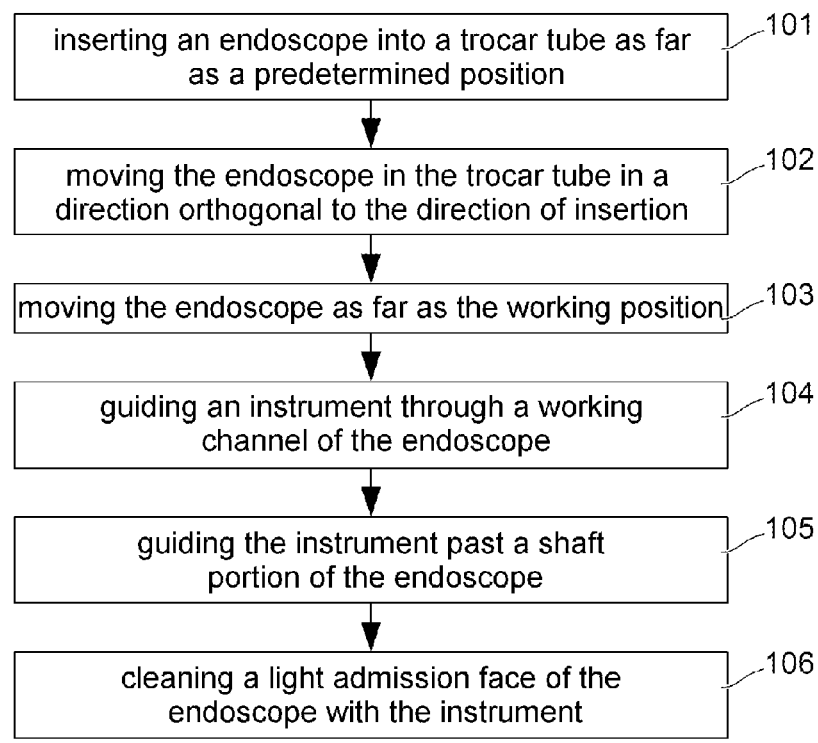
FIG. 15 is a schematic flow chart of a method for preparing for a use of an endoscopy system.

FIG. 15 shows a schematic flow chart of a method for preparing an endoscopy system for use. The method is also usable for endoscopy systems, or implementable with endoscopy systems, which differ from the endoscopy systems shown in FIGS. 1 to 14. Nonetheless, reference signs from FIGS. 1 to 14 are used below to make matters easier to understand.

In a first step 101, an endoscope 10 is inserted into a lumen 86 of a trocar tube 80 as far as a predetermined position. This predetermined position corresponds in particular to the position shown in FIG. 5.

In a second step 102, the endoscope 10 is moved in the lumen 86 of the trocar tube 80, and relative to the trocar tube, in a direction orthogonal to the direction of movement of the first step 101 and orthogonal to the longitudinal axes 28, 38, 48 of the endoscope 10 and to the longitudinal axis 88 of the trocar tube 80. In the second step 102, the endoscope 10 is moved relative to the trocar tube 80 in particular from the position shown in FIG. 5 to the position shown in FIG. 6.

In an optional third step 103, the endoscope 10 is moved relative to the trocar tube as far as a working position. The direction of movement of the third step 103 is in particular parallel to the direction of movement of the first step 101 and to the longitudinal axes 28, 38, 48 of the endoscope 10 and to the longitudinal axis 88 of the trocar tube 80. In the third step, a proximal shaft portion 40 can be inserted into the lumen 86 of the trocar tube 80. The third step 103 can in particular be omitted if the proximal shaft portion 40 of the endoscope 10 is not intended to be inserted into the lumen 86 of the trocar tube 80, or if the endoscope 10 has no proximal shaft portion 40.

In an optional fourth step 104, an instrument, for example a cleaning instrument 60, is guided partially through a working channel 50 of the endoscope 10. The direction of movement of the fourth step 104 corresponds in particular to the directions of movement of the first step 101 and of the third step 103 and is parallel to a longitudinal axis 58 of the working channel 50, parallel to a longitudinal axis 68 of the instrument 60 and in particular also parallel to a longitudinal axis 38 of a shaft portion 30 of the endoscope 10.

In a fifth step 105, the instrument 60 is guided partially past a shaft portion, in particular past a central shaft portion 30 of the endoscope 10. The direction of movement of the fifth step 105 corresponds to the direction of movement of the fourth step 104 and is in particular parallel to a longitudinal axis 38 of a shaft portion 30 of the endoscope 10. The fifth step 105 can follow on directly from the fourth step 104, such that the fourth step 104 transitions into the fifth step 105. At the end of the fifth step 105, a working or cleaning position of the instrument 60 is reached.

If the instrument 60 is a cleaning instrument, a light admission face 11 of the endoscope 10 can be cleaned in a sixth step 106. For this purpose, for example, deposits are wiped from the light admission face 11 by means of a wiping lip 72 moved across the light admission face 11, or they are flushed away from the light admission face 11 by means of a stream 75 of fluid formed by a nozzle 74. Alternatively, in the sixth step 106, a stream 75 of fluid that prevents the formation of deposits can be generated at the light admission face 11 of the endoscope 10.

While specific embodiments of the invention have been shown and described in detail to illustrate the application of the principles of the invention, it will be understood that the invention may be embodied otherwise without departing from such principles.

REFERENCE NUMBERS

- 10 endoscope
- 11 light admission face at the distal end 12 of the endoscope 10
- 12 distal end of the endoscope 10
- 13 endoscope shaft of the endoscope 10
- 14 manipulation facility at the proximal end 15 of the endoscope 10
- 15 proximal end of the endoscope 10
- 20 distal shaft portion of the shaft 13 of the endoscope 10
- 21 edge of the cross section of the distal shaft portion 20
- 28 longitudinal axis of the distal shaft portion 20
- 30 central shaft portion of the shaft 13 of the endoscope 10
- 31 first edge portion of the cross section of the central shaft portion 30
- 32 second edge portion of the cross section of the central shaft portion 30
- 34 proximal end of the central shaft portion 30
- 38 longitudinal axis of the central shaft portion 30
- 40 proximal shaft portion of the shaft 13 of the endoscope 10
- 41 edge of the cross section of the proximal shaft portion 40
- 48 longitudinal axis of the proximal shaft portion 40
- 50 working channel in the proximal shaft portion 40 and in the manipulation facility 14 of the endoscope 10, for receiving an instrument 60
- 52 sealing facility in the working channel 50 for fluid-tight sealing of the working channel 50 or for reducing the cross section thereof
- 53 outlet opening of the working channel 50 at the distal end of the proximal shaft portion 40
- 58 longitudinal axis of the working channel 50
- 60 cleaning instrument for cleaning the light admission face 11 of the endoscope 10
- 61 distal end of the cleaning instrument 60
- 63 instrument shaft of the cleaning instrument 60
- 64 wheel at the cleaning instrument 60, forming the proximal end of the cleaning instrument 60
- 68 longitudinal axis of the instrument shaft 63
- 70 cleaning tool at the distal end 61 of the cleaning instrument 60
- 72 wiping lip of the cleaning tool 70 for wiping deposits from the light admission face 11 of the endoscope 10
- 73 fluid channel in the instrument shaft 63
- 74 nozzle of the cleaning tool 70
- 75 stream of fluid formed at the light admission face 11 of the endoscope by the nozzle 74
- 76 hinge between the cleaning tool 70 and the instrument shaft 63 of the cleaning instrument 60
- 78 pivot axis of the hinge 76
- 80 trocar tube
- 81 proximal end of the trocar tube 80
- 82 distal end of the trocar tube 80
- 86 lumen of the trocar tube
- 88 longitudinal axis of the trocar tube 80
- 93 groove as guiding mechanism at the endoscope shaft 13 of the endoscope 10
- 96 web, corresponding to the groove 93, as guiding mechanism at the cleaning instrument 60
- 101 first step (inserting an endoscope into a trocar tube as far as a predetermined position)
- 102 second step (moving the endoscope in the trocar tube in a direction orthogonal to the direction of insertion)
- 103 third step (moving the endoscope as far as a working position)
- 104 fourth step (guiding an instrument through a working channel of the endoscope)
- 105 fifth step (guiding the instrument past a shaft portion of the endoscope)
- 106 sixth step (cleaning a light admission face of the endoscope)

What is claimed is:

1. An endoscopy system comprising:
    an endoscope, the endoscope comprising:
        an endoscope shaft with a distal shaft portion, a central shaft portion, and a proximal shaft portion; and
        a light admission face at the distal shaft portion, wherein a cross section of the central shaft portion is smaller than a cross section of the distal shaft portion, and the cross section of the central shaft portion is smaller than a cross section of the proximal shaft portion; and
    a cleaning instrument for cleaning or drying the light admission face, the cleaning instrument comprising:
        an instrument shaft; and
        a tool at a distal end of the instrument shaft for cleaning or drying the light admission face, wherein the instrument shaft is configured to be arranged beside the endoscope shaft, wherein the cross section of the proximal shaft portion is offset with respect to the cross section of the central shaft portion in a first direction that is opposite to or different from a second direction in which the cross section of the distal shaft portion is offset with respect to the cross section of the central shaft portion.

2. The endoscopy system according to claim 1, wherein:
    for each of the cross section of the central shaft portion, the cross section of the distal shaft portion, and the cross section of the proximal shaft portion, the cross section has a first edge point, a second edge point and an intersection point, a line between the first and second edge points intersects with a central longitudinal axis of the central shaft portion at the intersection point, and the lines between the first and second edge points parallel with each other;
    a distance between the first edge point and the intersection point of the distal shaft portion is same as a distance between the first edge point and the intersection point of the central shaft portion, a distance between the second edge point and the intersection point of the distal shaft portion is larger than a distance between the second edge point and the intersection point of the central shaft portion; and a distance between the first edge point and the intersection point of the proximal shaft portion is larger than a distance between the first edge point and the intersection point of the central shaft portion, a distance between the second edge point and the intersection point of the proximal shaft portion is same as a distance between the second edge point and the intersection point of the central shaft portion.

3. The endoscopy system according to claim 1, wherein:
a first peripheral surface of the central shaft portion is flush in a direction parallel to a longitudinal axis of the central shaft portion at a first side evenly with a peripheral surface of the distal shaft portion, and
a second peripheral surface of the central shaft portion is flush in the direction parallel to the longitudinal axis of the central shaft portion at a second side opposite the first side evenly with a peripheral surface of the proximal shaft portion.

4. The endoscopy system according to claim 1, wherein:
the distal shaft portion, the central shaft portion, and the proximal shaft portion do not share a central longitudinal axis;
a first edge of the central shaft portion in a direction parallel to a longitudinal axis of the central shaft portion aligns with a first edge of the distal shaft portion in the direction parallel to the longitudinal axis of the central shaft portion, a second edge of the central shaft portion in the direction parallel to the longitudinal axis of the central shaft portion aligns with a second edge of the proximal shaft portion in the direction parallel to the longitudinal axis of the central shaft portion, the first and second edges of the central shaft portion are different edges.

5. The endoscopy system according to claim 1, further comprising a fluid channel in the instrument shaft, wherein:
the tool comprises a nozzle connected to a distal end of the fluid channel; and
the nozzle is configured to convey a fluid to the light admission face of the endoscope.

6. The endoscopy system according to claim 5, wherein the nozzle is configured to form a stream of fluid directed toward the light admission face of the endoscope, at least either to remove a deposit on the light admission face or to prevent the development of a deposit on the light admission face.

7. The endoscopy system according to claim 1, further comprising a guiding mechanism for guiding the cleaning instrument at the endoscope shaft of the endoscope.

8. The endoscopy system according to claim 1, wherein the tool comprises a wiper for wiping away deposits at the light admission face of the endoscope.

9. The endoscopy system according to claim 8, wherein the tool has a hinge, which facilitates placement of a wiping lip of the wiper at a light admission face of the endoscope.

10. An endoscopy system comprising:
an endoscope, the endoscope comprising:
an endoscope shaft with a distal shaft portion, a central shaft portion, and a proximal shaft portion; and
a light admission face at the distal shaft portion, wherein a cross section of the central shaft portion is smaller than a cross section of the distal shaft portion, and the cross section of the central shaft portion is smaller than a cross section of the proximal shaft portion;
a cleaning instrument for cleaning or drying the light admission face, the cleaning instrument comprising:
an instrument shaft; and
a tool at a distal end of the instrument shaft for cleaning or drying the light admission face, wherein the instrument shaft is configured to be arranged beside the endoscope shaft;
a trocar tube with a lumen for receiving the endoscope shaft, wherein the endoscope shaft and the trocar tube are configured such that the distal shaft portion of the endoscope shaft can be guided completely through the trocar tube, wherein the trocar tube is not longer than the central shaft portion of the endoscope.

11. The endoscopy system according to claim 10, wherein the central shaft portion of the endoscope, the instrument shaft of the cleaning instrument, and the trocar tube are configured such that the cross section of the central shaft portion of the endoscope and a cross section of the instrument shaft of the cleaning instrument substantially fills a cross section of the lumen of the trocar tube.

12. An endoscopy system comprising:
an endoscope, the endoscope comprising:
an endoscope shaft with a distal shaft portion, a central shaft portion, and a proximal shaft portion; and
a light admission face at the distal shaft portion, wherein a cross section of the central shaft portion is smaller than a cross section of the distal shaft portion, and the cross section of the central shaft portion is smaller than a cross section of the proximal shaft portion; and
a cleaning instrument for cleaning or drying the light admission face, the cleaning instrument comprising:
an instrument shaft; and
a tool at a distal end of the instrument shaft for cleaning or drying the light admission face, wherein the instrument shaft is configured to be arranged beside the endoscope shaft, wherein:
a cross section of the instrument shaft is adapted to a cross section of a central shaft portion of the endoscope such that a total cross section of a parallel arrangement of the instrument shaft and of the central shaft portion of the endoscope is not greater than a cross section of a distal shaft portion of the endoscope.

* * * * *